United States Patent [19]

Cantatore

[11] 4,369,321
[45] Jan. 18, 1983

[54] PIPERIDINE DERIVATIVES WHICH ARE STABILIZERS FOR SYNTHETIC POLYMERS

[75] Inventor: Giuseppe Cantatore, Casalecchio di Reno, Italy

[73] Assignee: Chimosa Chimica Organica S.p.A., Bologna, Italy

[21] Appl. No.: 215,925

[22] Filed: Dec. 12, 1980

[30] Foreign Application Priority Data

Dec. 21, 1979 [IT] Italy ............................ 28324 A/79

[51] Int. Cl.³ ................. C07D 401/12; C07D 403/12; C07D 413/12
[52] U.S. Cl. .................................... 546/187; 546/188; 544/130; 544/360; 260/244.4
[58] Field of Search ..................... 260/244.4; 546/187, 546/188; 544/130, 360

[56] References Cited

U.S. PATENT DOCUMENTS

| | | | |
|---|---|---|---|
| 4,021,432 | 5/1977 | Holt et al. | 546/188 |
| 4,049,647 | 9/1977 | Holt et al. | 546/187 X |
| 4,102,858 | 7/1978 | Minagawa et al. | 546/187 X |
| 4,198,334 | 4/1980 | Rasberger | 546/188 X |
| 4,265,805 | 5/1981 | Thomas | 546/188 X |
| 4,278,683 | 7/1981 | Stoltefuss et al. | 546/188 X |

FOREIGN PATENT DOCUMENTS

| | | |
|---|---|---|
| 2183293 | 12/1973 | France . |
| 2183294 | 12/1973 | France . |
| 2405247 | 5/1979 | France . |
| 1326889 | 8/1973 | United Kingdom . |
| 1578043 | 10/1980 | United Kingdom . |

*Primary Examiner*—John M. Ford
*Attorney, Agent, or Firm*—Wenderoth, Lind & Ponack

[57] ABSTRACT

The invention relates to new piperidine compounds which act as light stabilizers, heat stabilizers and oxidation stabilizers for synthetic polymers, in particular for hydrocarbon polymers. The compounds are piperidinol carbamates of the formula:

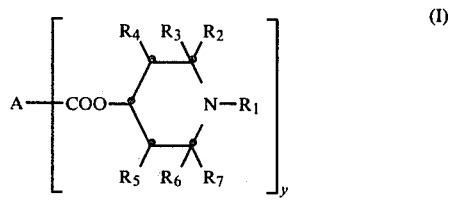

in which $R_1$, $R_2$, $R_3$, $R_4$, $R_5$, $R_6$, $R_7$ and A have the meanings defined in the description and y is an integer from 1 to 4. In particular, A represents a monovalent to tetravalent radical, always bonded to the carboxypiperidine radicals via nitrogen atoms.

4 Claims, No Drawings

PIPERIDINE DERIVATIVES WHICH ARE STABILIZERS FOR SYNTHETIC POLYMERS

The present invention relates to novel piperidine compounds which can be used as light stabilisers, heat stabilisers and oxidation stabilisers for synthetic polymers, and to the process for their preparation.

More precisely, the present invention relates to novel piperidine esters of carbamic acid, of the formula

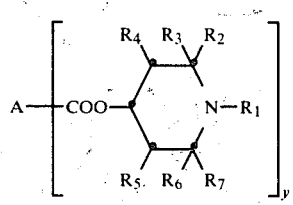

and acid addition salts thereof,
in which $R_1$ represents hydrogen, $C_1$-$C_{12}$-alkyl, —$CH_2CN$, $C_3$-$C_{12}$-alkenyl or -alkinyl, benzyl, benzyl substituted by 1 to 3 $C_1$-$C_4$-alkyl radicals, hydroxybenzyl or hydroxybenzyl substituted by 1 to 3 $C_1$-$C_4$-alkyl radicals; a —$COR_8$, —$COOR_8$, —$CH_2COOR_8$ or —$CONR_8R_9$ radical, in which $R_8$ and $R_9$, which may be identical or different, represent linear or branched $C_1$-$C_{12}$-alkyl, $C_3$-$C_{12}$-alkenyl, $C_5$-$C_{12}$-cycloalkyl, phenyl, phenyl substituted by 1 to 3 $C_1$-$C_8$-alkyl radicals, hydroxyphenyl, hydroxyphenyl substituted by 1 to 3 $C_1$-$C_8$-alkyl radicals, $C_7$-$C_{12}$-aralkyl, 2,2,6,6-tetramethyl-piperidin-4-yl, 1,2,2,6,6-pentamethyl-piperidin-4-yl or, when they are bonded to N, can be hydrogen or together with the N to which they are bonded can form a 5-7-membered heterocyclic ring containing a nitrogen atom; or $R_1$ represents a

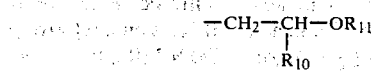

radical, in which $R_{10}$ is hydrogen, methyl or phenyl and $R_{11}$ is hydrogen, —$R_8$, —$COR_8$ or —$CONR_8R_9$, in which $R_8$ and $R_9$ are as defined above; or $R_1$ represents a

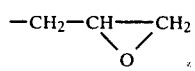

radical; $R_2$, $R_3$, $R_6$ and $R_7$, which may be identical or different, are alkyl containing 1 to 6 C atoms; $R_4$ and $R_5$, which may be identical or different, are hydrogen or alkyl containing 1 to 6 C atoms; and y represents an integer from 1 to 4.

If $y=1$, A is a

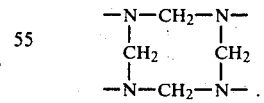

radical, in which $R_{12}$ is a radical of the formula (II)

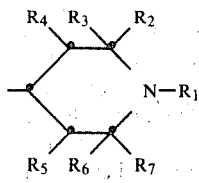

in which $R_1$, $R_2$, $R_3$, $R_4$, $R_5$, $R_6$ and $R_7$ have the above meanings, and $R_{13}$ is hydrogen or linear or branched $C_1$-$C_{20}$-alkyl, $C_5$-$C_{12}$-cycloalkyl, substituted or unsubstituted $C_6$-$C_{20}$-aryl, substituted or unsubstituted $C_7$-$C_{20}$-aralkyl or a group of formula (II), or A is a radical of a 5-7-membered heterocyclic compound containing a nitrogen atom in the ring and with the free valency on the nitrogen.

If $y=2$, A is a radical of the formula (III)

in which $R_{14}$ and $R_{15}$, which may be identical or different, are $C_5$-$C_{12}$-cycloalkyl or a radical of the formula (II), and $R_{16}$ is $C_1$-$C_{20}$-alkylene, $C_5$-$C_{12}$-cycloalkylene, $C_6$-$C_{12}$-arylene or $C_7$-$C_{12}$-aralkylene; or A is a bivalent radical of a 5-7-membered heterocyclic compound containing 2 nitrogen atoms in the ring, with the free valencies on the two nitrogen atoms.

If $y=3$, A is a radical of the formula (IV)

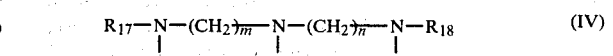

in which $R_{17}$ and $R_{18}$ may be identical or different and represent $C_1$-$C_{12}$alkyl, $C_5$-$C_{12}$cycloalkyl or a radical of the formula (II) and m and n, which may be identical or different, are integers from 2 to 6, or A is a trivalent radical of a 6-7-membered heterocyclic compound containing 3 nitrogen atoms in the ring, with the free valencies on the three nitrogen atoms.

If $y=4$, A is a radical of the formula (V)

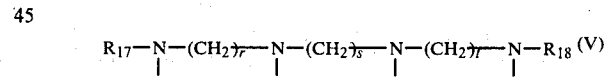

in which $R_{17}$ and $R_{18}$ have the abovementioned meanings and r, s and t, which may be identical or different, represent integers from 2 to 6, or A is a radical $$\begin{array}{c} -N-CH_2-N- \\ | \quad\quad\quad | \\ CH_2 \quad\quad CH_2 \\ | \quad\quad\quad | \\ -N-CH_2-N- \end{array}.$$

Examples which particularly illustrate the meanings of the various radicals are as follows:

$R_1$: hydrogen, methyl, cyanomethyl, ethyl, n-propyl, n-butyl, isobutyl, n-hexyl, n-octyl, n-decyl, n-dodecyl, allyl, 2-butenyl, 10-undecenyl, propargyl, benzyl, 4-methylbenzyl, 4-t-butylbenzyl, 4-hydroxybenzyl and 3,5-di-t-butyl-4-hydroxybenzyl.

$R_8$ and $R_9$: methyl, ethyl, n-propyl, n-butyl, n-hexyl, n-octyl, n-decyl, n-dodecyl, allyl, 2-butenyl, 10-undecenyl, cyclohexyl, 2- and 4-methylcyclohexyl, 3,3,5-trimethylcyclohexyl, phenyl, 2- and 4-methylphenyl, 2,4- and 2,6-dimethylphenyl, 4-t-butylphenyl, 3,5-di-t-butyl-4-hydroxyphenyl, benzyl, 4-methylbenzyl, 4-t-butylbenzyl, 2,2,6,6-tetramethyl-piperidin-4-yl and 1,2,2,6,6-pentamethyl-piperidin-4-yl; furthermore, when $R_8$ and $R_9$ are bonded to a N, they are preferably hydrogen or, together with the N atom to which they are bonded, form part of, for example, a pyrrolidine, piperidine, morpholine, piperazine, N-methylpiperazine, homopiperazine or N-methylhomopiperazine ring.

The group

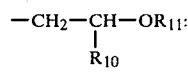

—$CH_2CH_2OH$, —$CH_2CH(OH)CH_3$, —$CH_2CH(OH)C_6H_5$, —$CH_2CH_2OC_2H_5$, —$CH_2CH_2OC_4H_9$, —$CH_2CH_2OCOCH_3$, —$CH_2CH_2OCOC_3H_7$, —$CH_2CH_2OCON(CH_3)_2$ and —$CH_2CH_2OCON(C_2H_5)_2$.

$R_2$, $R_3$, $R_6$ and $R_7$: methyl and ethyl.

$R_4$ and $R_5$: hydrogen and methyl.

$R_{12}$: 2,2,6,6-tetramethyl-piperidin-4-yl, 1,2,2,6,6-pentamethyl-piperidin-4-yl, 1-allyl-2,2,6,6-tetramethyl-piperidin-4-yl, 1-benzyl-2,2,6,6-tetramethyl-piperidin-4-yl, 1-acetyl-2,2,6,6-tetramethyl-piperidin-4-yl.

$R_{13}$: hydrogen, methyl, ethyl, n-propyl, isopropyl, n-butyl, isobutyl, n-hexyl, n-heptyl, n-octyl, n-decyl, n-dodecyl, n-hexadecyl, n-octadecyl, cyclohexyl, 2- and 4-methylcyclohexyl, 3,3,5-trimethylcyclohexyl, cyclooctyl, cyclododecyl, phenyl, o-, m- and p-toluyl, o-, m- and p-hydroxyphenyl, 3,5-di-t-butyl-4-hydroxy-phenyl, o-, m- and p-methoxyphenyl, o-, m- and p-ethoxyphenyl, benzyl, 4-methylbenzyl, 4-t-butylbenzyl, 4-hydroxybenzyl, 3,5-di-t-butyl-4-hydroxybenzyl, 4-methoxybenzyl, 4-ethoxybenzyl, 2,2,6,6-tetramethyl-piperidin-4-yl, 1,2,2,6,6-pentamethyl-piperidin-4-yl, 1-allyl-2,2,6,6-tetramethyl-piperidin-4-yl, 1-benzyl-2,2,6,6-tetramethyl-piperidin-4-yl and 1-acetyl-2,2,6,6-tetramethyl-piperidin-4-yl.

$R_{14}$, $R_{15}$: cyclohexyl, 3,3,5-trimethylcyclohexyl, 2,2,6,6-tetramethylpiperidin-4-yl, 1,2,2,6,6-pentamethyl-piperidin-4-yl, 1-allyl-2,2,6,6-tetramethyl-piperidin-4-yl, 1-benzyl-2,2,6,6-tetramethyl-piperidin-4-yl, 1-acetyl-2,2,6,6-tetramethyl-piperidin-4-yl.

$R_{16}$: methylene, ethylene, 1,2-propylene, trimethylene, tetramethylene, pentamethylene, hexamethylene, decamethylene, dodecamethylene, cyclohexylene, cyclohexylenedimethylene, o-, m- and p-phenylene and o-, m- and p-xylylene.

$R_{17}$, $R_{18}$: methyl, ethyl, n-propyl, isopropyl, n-butyl, 2-butyl, isobutyl, n-hexyl, n-heptyl, n-octyl, n-decyl, n-dodecyl, cyclohexyl, 3,3,5-trimethylcyclohexyl, 2,2,6,6-tetramethyl-piperidin-4-yl, 1,2,2,6,6-pentamethyl-piperidin-4-yl, 1-allyl-2,2,6,6-tetramethyl-piperidin-4-yl, 1-benzyl-2,2,6,6-tetramethyl-piperidin-4-yl, 1-acetyl-2,2,6,6-tetramethyl-piperidin-4-yl.

m, n, r, s and t are preferably 2, 3 or 6.

If $y=1$ and A is the radical of a heterocyclic compound containing a nitrogen atom, preferred examples are pyrrolidin-1-yl, piperidin-1-yl, morpholin-4-yl, piperazin-1-yl, 4-methyl-piperazin-1-yl, hexahydroazepin-1-yl, homopiperazin-1-yl and 4-methyl-homopiperazin-1-yl.

If $y=2$ and A is the radical of a heterocyclic compound containing two nitrogen atoms, preferred examples are:

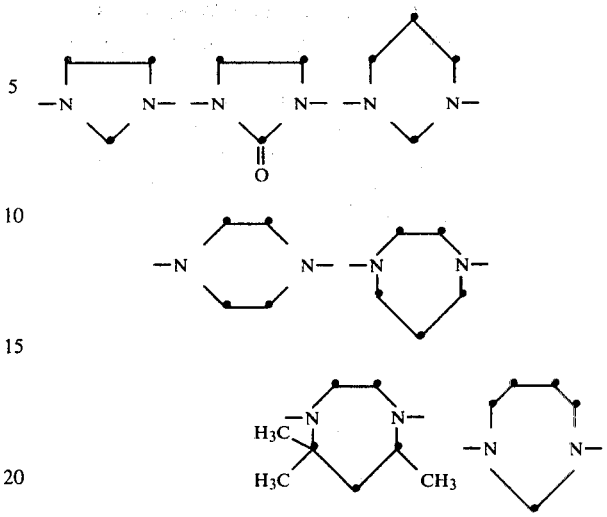

If $y=3$ and A is the radical of a heterocyclic compound containing 3 nitrogen atoms, preferred examples are:

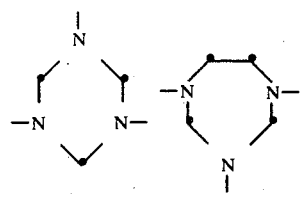

The present invention embraces also the salts of compounds of formula (I) which are formed by the addition of acids in amounts at most equivalent to the basic piperidine groups. Such acids can be inorganic acids such as sulfuric, hydrochloric or phosphoric acid, or organic acids such as carboxylic acids, sulfonic acids, phosphonic acids or phosphinic acids. If $R_1$ is an acyl group, such as —$COR_8$, —$COOR_8$ or —$CONR_8R_9$, the piperidine group is not basic and no stable salts are formed.

The novel piperidine compounds according to the present invention can be prepared (a) by trans-esterification of a piperidinol of the formula (VI)

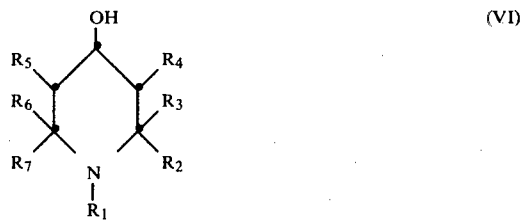 (VI)

with an ester of the formula (VII)

 (VII)

in which $R_{19}$ is $C_1$–$C_4$-alkyl or phenyl, preferably methyl or ethyl, in the presence of a trans-esterification catalyst, for example an alkali metal alkoxide, such as sodium methoxide or potassium tert.-butoxide, $LiNH_2$, an Al alkoxide, such as Al isopropoxide, a tetraalkyl titanate, such as tetrabutyl titanate, dibutyl-tin oxide or $Sb_2O_3$, in the presence or absence of a solvent, at a temperature of between 100° and 250° C. and at a pressure of between 0.1 and 760 mm Hg, or (b) by reaction of a chlorocarbonate of the formula (VIII)

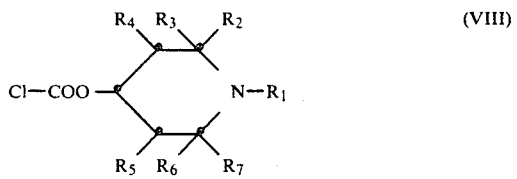

or the hydrochloride thereof with an amine of the formula (IX)

$$A\text{—}[H]_y \qquad (IX)$$

in the presence of an inorganic base, such as sodium or potassium bicarbonate or carbonate, sodium hydroxide or potassium hydroxide, or of an organic base, such as pyridine, triethylamine or tributylamine, in the presence or absence of a solvent, at a temperature of between −30° and 100° C., preferably at between −10° and 60° C.

For better illustration of the present invention, some examples of the preparation of the compounds of the formula (I) are given below; these examples are purely illustrative and do not imply any limitation.

EXAMPLE 1

A solution of 1 g of sodium in 30 ml of methanol is added to 56.8 g (0.2 mol) of N-butyl-N-ethoxycarbonyl-2,2,6,6-tetramethyl-4-piperidylamine and 34.54 g (0.22 mol) of 2,2,6,6-tetramethyl-4-hydroxypiperidine.

The mixture is heated to 180° C. whilst removing the methanol and the ethanol liberated in the reaction; the reaction mixture is then kept at 180°–190° C. for 6 hours. Thereafter it is poured into water and the precipitate obtained is filtered off, washed with water, dried and crystallised from methanol. This gives the compound of the formula:

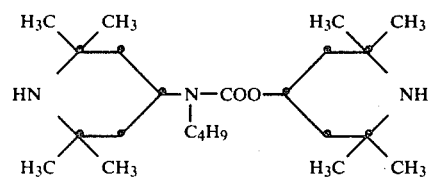

which melts at 80°–81° C.

Analysis for $C_{23}H_{45}N_3O_2$: calculated: C 69.83%; H 11.46%; N 10.62%; found: C 69.10%; H 11.34%; N 10.38%

The N-butyl-N-ethoxycarbonyl-2,2,6,6-tetramethyl-4-piperidylamine is prepared by reacting N-butyl-2,2,6,6-tetramethyl-4-piperidylamine with ethyl chlorocarbonate at 15°–25° C. in toluene in the presence of an aqueous solution of $K_2CO_3$. The product obtained, which is 99.2% pure, is employed directly, without any purification.

EXAMPLE 2

68 g (0.2 mol) of N-octyl-N-ethoxycarbonyl-2,2,6,6-tetramethyl-4-piperidylamine and 34.54 g (0.22 mol) of 2,2,6,6-tetramethyl-4-hydroxypiperidine are added to a solution of 1 g of sodium in a mixture of 100 ml of xylene and 30 ml of methanol, and the batch is heated to 140° C. whilst removing the methanol and the ethanol liberated in the reaction. After 1 hour at 140° C., the temperature is raised to 180° C., the xylene being distilled, and is kept at 180°–190° C. for 6 hours. After cooling, 200 ml of xylene are added to the reaction mixture, the batch is filtered to remove the catalyst, and the filtrate is washed repeatedly with water until the latter has a pH of 8, and is then evaporated to dryness. The oily residue obtained is dissolved in hexane and the solution is cooled to −10° C.; the crystalline precipitate obtained is filtered off and is recrystallised from hexane.

This gives the compound of the formula:

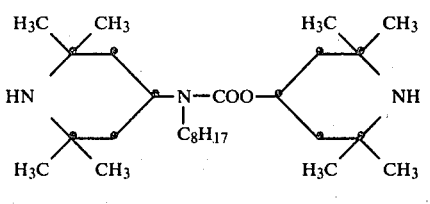

melting at 75°–6° C.

Analysis for $C_{27}H_{53}N_3O_2$: calculated: C 71.79%; H 11.83%; N 9.30%; found: C 71.71%; H 12.01%; N 9.27%

The N-octyl-N-ethoxycarbonyl-2,2,6,6-tetramethyl-4-piperidylamine is prepared by reacting N-octyl-2,2,6,6-tetramethyl-4-piperidylamine with ethyl chlorocarbonate at 10°–25° C. in toluene in the presence of an aqueous solution of $K_2CO_3$. The product obtained, which has a purity of 99.5%, is employed directly without any purification.

EXAMPLE 3

The compound of the formula

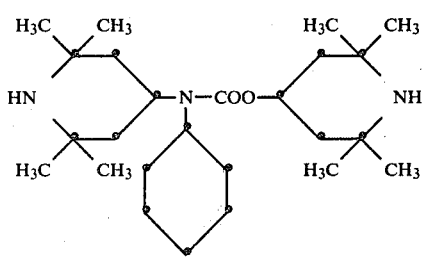

melting at 148°–9° C. (after recrystallisation from octane), and having the following analytical data calculated for $C_{25}H_{47}N_3O_2$: C 71.21%; H 11.23%; N 9.96%; found: C 70.24%; H 11.19%; N 9.89% is prepared in accordance with the process described in Example 2, from N-cyclohexyl-N-ethoxycarbonyl-2,2,6,6-tetramethyl-4-piperidylamine.

This last-mentioned compound was obtained by reacting N-cyclohexyl-2,2,6,6-tetramethyl-4-piperidylamine with ethyl chlorocarbonate in toluene in the presence of aqueous NaOH. The product obtained has a purity of 95% and is employed after crystallisation from hexane.

EXAMPLE 4

The compound of the formula

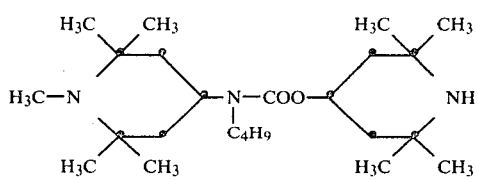

melting at 71°-2° C. (after recrystallisation from acetone) and having the following analytical data calculated for $C_{24}H_{47}N_3O_2$: C 70.37%; H 11.56%; N 10.26%; found: C 70.17%; H 11.46%; N 10.10% is prepared in accordance with the process described in Example 2, starting from N-butyl-N-ethoxycarbonyl-1,2,2,6,6-pentamethyl-4-piperidylamine, which itself is obtained by reacting N-butyl-1,2,2,6,6-pentamethyl-4-piperidylamine with ethyl chlorocarbonate.

The product obtained, having a purity of 99.3%, was employed directly.

EXAMPLE 5

99.2 g (0.2 mol) of N,N'-bis-(ethoxycarbonyl)-N,N'-bis-(2,2,6,6-tetramethyl-piperidin-4-yl)-trimethylenediamine and 69.1 g (0.44 mol) of 2,2,6,6-tetramethyl-4-hydroxypiperidine are added to a solution of 2 g of sodium in a mixture of 100 ml of xylene and 50 ml of methanol and the batch is heated to 140° C., whilst removing the methanol and the ethanol liberated in the reaction and part of the xylene, and is kept at this temperature for 1 hour. The temperature is then raised to 180° C. after the solvent has been distilled, and is kept at 180°-190° C. for 6 hours. Finally the mixture is heated for 30 minutes at 160°-180° C. under reduced pressure (about 100 mm Hg). The reaction mixture obtained is dissolved in 300 ml of xylene, the solution is filtered and the filtrate is washed repeatedly with water until the pH of the latter is 8, and is evaporated to dryness.

The compound of the formula:

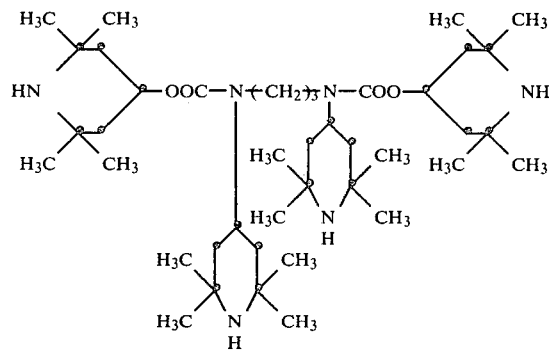

melting at 51°-52° C., is obtained.

Analysis for $C_{41}H_{78}N_6O_4$: calculated: C 68.48%; H 10.93%; N 11.69% found: C 68.10%; H 11.02%; N 11.44%

The N,N'-bis-(ethoxycarbonyl)-N,N'-bis-(2,2,6,6-tetramethyl-piperidin-4-yl)-trimethylenediamine was obtained by reacting N,N'-bis-(2,2,6,6-tetramethyl-piperidin-4-yl)-trimethylenediamine with ethyl chlorocarbonate in toluene in the presence of aqueous NaOH. The product obtained has a purity of 99% and is employed directly without any purification.

EXAMPLE 6

A solution of 2 g of sodium in 50 ml of methanol is added to 107.6 g (0.2 mol) of N,N'-bis-(ethoxy-carbonyl)-N,N'-bis-(2,2,6,6-tetramethyl-piperidin-4-yl)-hexamethylenediamine and 69.1 g (0.44 mol) of 2,2,6,6-tetramethyl-4-hydroxypiperidine. The mixture is heated to 180° C. whilst removing the methanol, and the ethanol formed in the reaction and is then kept at 180° C. for 8 hours. Finally it is heated at 160°-180° C. under reduced pressure (about 100 mm Hg) for 30 minutes. After cooling to 80° C., the reaction mixture is dissolved in 300 ml of xylene, the solution is filtered and the filtrate is evaporated to dryness.

The residue obtained is washed repeatedly with water until the latter is at pH 8, and is dried and crystallised from hexane.

The compound of the formula

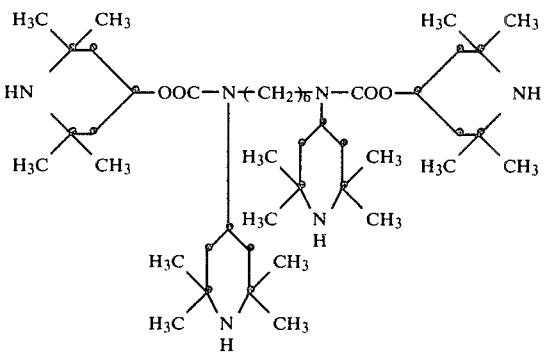

melting at 148°-9° C. is obtained.

Analysis for $C_{44}H_{84}N_6O_4$: calculated: C 69.43%; H 11.12%; N 11.04%; found: C 69.18%; H 11.13%; N 10.71%

The N,N'-bis-(ethoxycarbonyl)-N,N'-bis-(2,2,6,6-tetramethyl-piperidin-4-yl)-hexamethylenediamine was prepared by reacting N,N'-bis-(2,2,6,6-tetramethyl-piperidin-4-yl)-hexamethylenediamine with ethyl chlorocarbonate in toluene in the presence of aqueous NaOH and was crystallised from octane.

EXAMPLE 7

The compound of the formula:

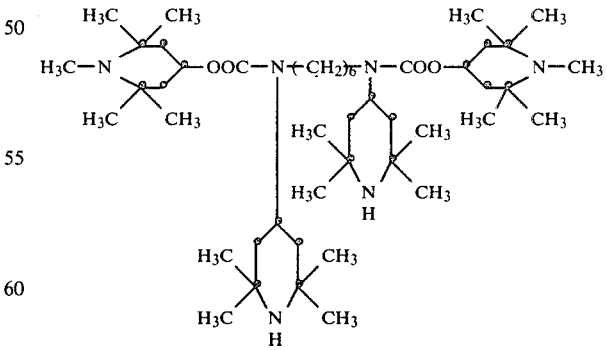

melting at 183°-5° C. (after recrystallisation from octane) and having the following analytical data:

calculated for $C_{46}H_{88}N_6O_4$: C 70.00%; H 11.24%; N 10.65%; found: C 68.77%; H 11.03%; N 10.38% is prepared in accordance with the process described in Example 6, starting from N,N'-bis-(ethoxycarbonyl)-N,N'-bis-(2,2,6,6-tetramethylpiperidin-4-yl)-hexamethylene-diamine and 1,2,2,6,6-pentamethyl-4-hydroxypiperidine.

EXAMPLE 8

92 g (0.4 mol) of N,N'-bis-(ethoxycarbonyl)-piperazine, prepared in accordance with J. ORG. CHEM. 25, 1874 (1960) and 131.9 g (0.84 mol) of 2,2,6,6-tetramethyl-4-hydroxypiperidine are added to a solution of 2 g of sodium in a mixture of 200 ml of xylene and 40 ml of methanol.

The mixture is heated to 180° C. in 1 hour, whilst removing the volatile components, and is kept at 180°–190° C. for 6 hours. After cooling to ambient temperature, 400 ml of chloroform are added and the mixture is stirred for 30 minutes and filtered. The filtrate is evaporated to dryness and the residue obtained is crystallised twice from xylene.

The compound of the formula:

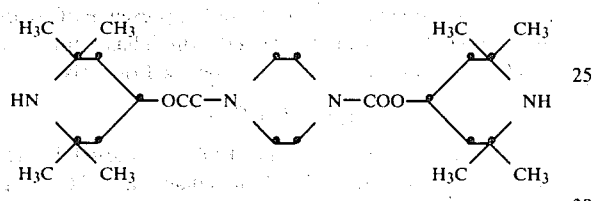

melting at 208°–9° C. is obtained.

Analysis for $C_{24}H_{44}N_4O_4$: calculated: C 63.68%; H 9.80%; N 12.38%; found: C 63.24%; H 9.65%; N 12.39%

EXAMPLE 9

60.6 g (0.2 mol) of 1,3,5-tris-(ethoxycarbonyl)-hexahydro-1,3,5-triazine (prepared according to J. Heterocycl. Chem. 1974, 11(6), 937) and 103.6 g (0.66 mol) of 2,2,6,6-tetramethyl-4-hydroxypiperidine are added to a solution of 2 g of sodium in a mixture of 100 ml of xylene and 30 ml of methanol.

The mixture is heated to 180° C., whilst removing the volatile products, and is kept at 180°–190° C. for 6 hours; it is finally heated for 1 hour at 150°–160° C. under reduced pressure (about 100 mm Hg). 300 ml of xylene are added to the cold mixture and the batch is filtered to remove the insoluble materials. The filtrate is stirred for 30 minutes at ambient temperature with 50 ml of water; a crystalline precipitate forms, which is filtered off, washed with water, dried and recrystallised from octane.

The compound of the formula:

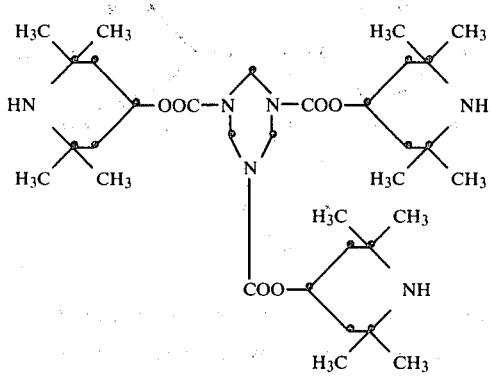

melting at 180°–181° C. is obtained.

Analysis for $C_{33}H_{60}N_6O_6$: calculated: C 62.24%; H 9.49%; N 13.20%; found: C 61.41%; H 9.26%; N 12.89%

EXAMPLE 10

60.6 g (0.2 mol) of 1,3,5-tris-(ethoxycarbonyl)-hexahydro-1,3,5-triazine and 112.9 g (0.66 mol) of 1,2,2,6,6-pentamethyl-4-hydroxypiperidine are added to a solution of 2 g of sodium in a mixture of 100 ml of xylene and 30 ml of methanol, and the batch is heated to 180° C. whilst removing the volatile products and is kept at 180°–190° C. for 6 hours.

After cooling, 300 ml of xylene are added and the mixture is filtered; the filtrate is washed repeatedly with water until the pH of the latter is neutral and is then evaporated to dryness.

The residue obtained is crystallised from acetone.

The compound of the formula

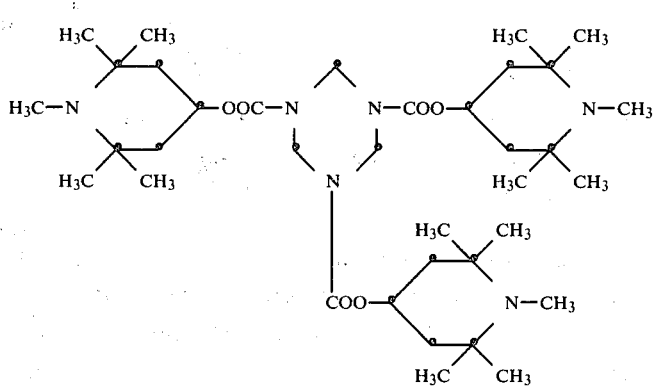

melting at 133°–4° C. is obtained.

Analysis for $C_{36}H_{66}N_6O_6$: calculated: C 63.68%; H 9.80%; N 12.38%; found: C 63.59%; H 9.84%; N 12.24%

EXAMPLE 11

The compound of the formula

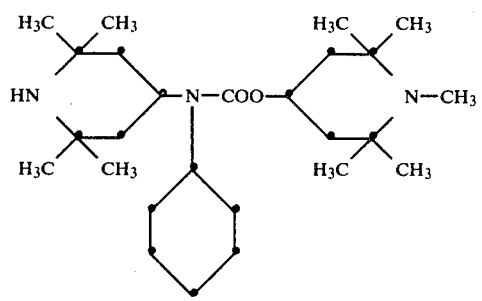

melting at 102°–3° C. (after recrystallisation from hexane) and having the following analytical data:

calculated for $C_{26}H_{49}N_3O_6$: C 71.68%; H 11.34%; N 9.64%; found: C 71.60%; H 11.50%; N 9.66% is prepared in accordance with the process described in Example 2, starting from N-cyclohexyl-N-ethoxycarbonyl-2,2,6,6-tetramethyl-4-piperidylamine and 1,2,2,6,6-pentamethyl-4-hydroxy-piperidine.

EXAMPLE 12

45.2 g (0.1 mol) of the compound described in Example 8, 40.8 g (0.4 mol) of acetic anhydride and 80.8 g (0.8 mol) of triethylamine are heated under reflux for 15 hours and the mixture is then filtered hot. The crystalline precipitate obtained is recrystallised from toluene.

The compound of the formula

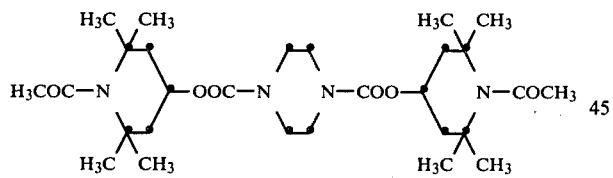

melting at 179°–80° C. is obtained.

Analysis for $C_{28}H_{48}N_4O_6$: calculated: C 62.66%; H 9.01%; N 10.44%; found: C 62.51%; H 9.05%; N 10.30%

EXAMPLE 13

A mixture of 36.7 g (0.1 mol) of N-ethoxycarbonyl-bis-(2,2,6,6-tetramethyl-4-piperidinyl)-amine, 17.22 g (0.11 mol) of 2,2,6,6-tetramethyl-4-hydroxypiperidine and 1 g sodium methoxide is heated for 7 hours to 200° C. and for 2 hours to 160°–170° C. at a vacuum of 100 mm Hg. After cooling the product is ground, washed with water, dried and recrystallised from acetone.

In this way the compound of formula

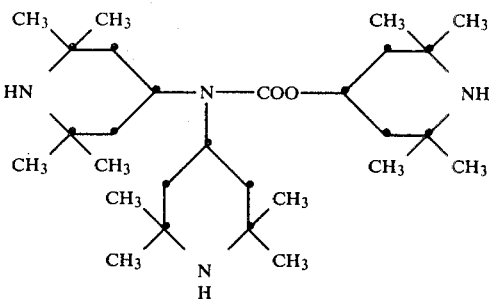

is obtained, melting at 187°–8° C.

Analysis ($C_{28}H_{54}N_4O_2$): calculated: C 70.25%; H 11.37%; N 11.70%; found: C 69.50%; H 11.43%; N 11.57%

The N-ethoxycarbonyl-bis(2,2,6,6-tetramethyl-4-piperidyl)-amine is prepared by reacting bis(2,2,6,6-tetramethyl-4-piperidyl)-amine with ethyl chlorocarbonate in chloroform at 10°–20° C. in the presence of aqueous NaOH. The product obtained, which has a purity of 99.2% and melts at 117° C., can be used directly.

EXAMPLE 14

A mixture of 36.8 g (0.1 mol) of N,N'-dicyclohexyl-N,N'-bis(ethoxycarbonyl)-ethylenediamine, 34.54 g (0.22 mol) of 2,2,6,6-tetramethyl-4-hydroxypiperidine and 1 g sodium methoxide is heated 4 hours to 190°–200° C. and 2 hours to 160°–180° C./100 mm Hg. After cooling the reaction mixture is ground, washed with water, dried and recrystallised from toluene.

There is obtained the compound of formula

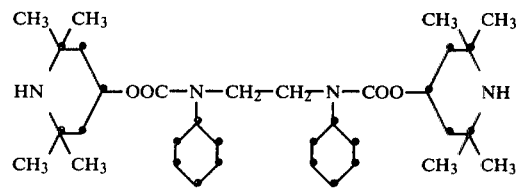

melting at 210°–211° C.

Analysis ($C_{34}H_{62}N_4O_4$): calculated: C 69.11%; H 10.58%; N 9.48%; found: C 69.34%; H 10.51%; N 9.42%

The N,N'-dicyclohexyl-N,N'-bis(ethoxycarbonyl)-ethylenediamine (m.p. 108° C.) is prepared by reacting N,N'-dicyclohexylethylenediamine with ethyl chlorocarbonate in chloroform at 10°–20° C. in the presence of aqueous NaOH. The obtained product has a purity of 99.7% and is used directly.

EXAMPLE 15

A mixture of 48.3 g (0.1 mol) of N,N'-dicyclohexyl-N,N'-N'''-tris(ethoxycarbonyl)-diethylenetriamine, 62.8 g (0.4 mol) of 2,2,6,6-tetramethyl-4-hydroxypiperidine and 2 g of NaOCH$_3$ is heated to 200° C. for 8 hours at normal pressure and for further 8 hours under vacuum (up to 100 mm Hg). After cooling the reaction mixture is ground, washed with water, dried and recrystallised from xylene.

There is obtained the compound of formula

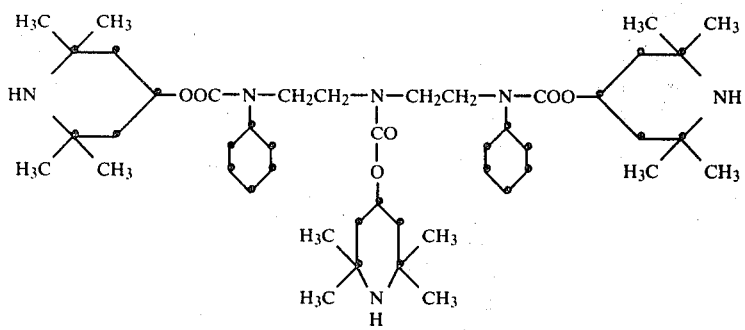

melting at 184°–185° C.

Analysis (C₄₆H₈₄N₆O₆) calculated: C 67.61%; H 10.36%; N 10.28%; found: C 67.22%; H 10.29%; N 10.08%

The N,N′-dicyclohexyl-N,N′,N″-tris(ethoxycarbonyl)-diethylenetriamine (m.p. 60°–61° C., from hexane) is prepared by reacting N,N′-dicyclohexyldiethylenetriamine with ethyl chlorocarbonate in toluene at 10°–20° C. in the presence of aqueous NaOH.

EXAMPLE 16

The compound described in example 7 may alternatively be prepared by reacting the hydrochloride of 1,2,2,6,6-pentamethylpiperidin-4-yl chlorocarbonate with N,N′-bis(2,2,6,6-tetramethylpiperidin-4-yl)-hexamethylenediamine according to the following procedure.

A solution of 28.3 g (0.105 mol) of the hydrochloride of 1,2,2,6,6-pentamethylpiperidin-4-yl chlorocarbonate in 70 ml of chloroform is added to a solution of 19.7 g (0.05 mol) of N,N′-bis(2,2,6,6-tetramethylpiperidin-4-yl)-hexamethylenediamine in 50 ml of chloroform cooled to 0° C. During the addition the temperature is kept below 10° C. After the addition the reaction mixture is stirred for 1 hour at a temperature of about 10° C., then a solution of 8.8 g NaOH in 50 ml of water is added during 40 minutes under stirring keeping the temperature at about 10° C. After further 4 hours stirring at room temperature the aqueous layer is separated off, the chloroform solution is dried over Na₂SO₄ and evaporated to dryness. The obtained residue is crystallised from octane yielding a product melting at 186°–188° C.

The used chlorocarbonate hydrochloride is prepared by addition of a solution of 148.5 g of phosgene in 400 ml of acetonitrile to a suspension of 207.5 g of the hydrochloride of 1,2,2,6,6-pentamethyl-4-hydroxypiperidine in 400 ml of acetonitrile at a temperature of 0° C. After 15 hours stirring the mixture at room temperature the temperature is slowly raised to 50° C. By passing a stream of nitrogen during 6 hours at 50° C. the excess of phosgene is removed. Finally the solvent is evaporated in vacuo at 50° C. The obtained residue is the pure product melting at 153°–156° C.

EXAMPLE 17

22.8 g (0.1 mol) of N-ethoxycarbonyl-2,2,6,6-tetramethyl-4-piperidylamine, 34.54 g (0.22 mol) of 2,2,6,6-tetramethyl-4-hydroxypiperidine and 1 g of NaOCH₃ are heated to 180° C. for 6 hours at normal pressure and for 1 hour at about 100 mm Hg. After cooling the obtained mixture is ground, washed with water and recrystallised from isopropanol.

The obtained compound of formula

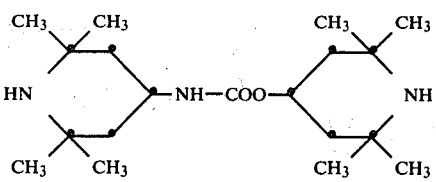

melts at 182°–183° C.

Analysis (C₁₉H₃₇N₃O₂) calculated: C 67.21%; H 10.98%; N 12.38%; found: C 66.85%; H 10.93%; N 12.48%

EXAMPLE 18

The compound of the formula

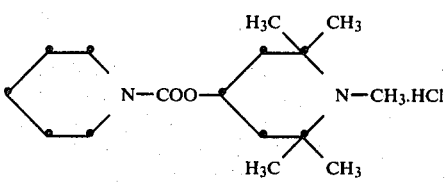

is prepared by reacting 8.5 g (0.1 mol) of piperidine dissolved in 50 ml chloroform with 29.7 g (0.11 mol) of the hydrochloride of 1,2,2,6,6-pentamethylpiperidin-4-yl chlorocarbonate dissolved in 70 ml chloroform at a temperature of 0° to 10° C. and adding a solution of 4.4 g (0.11 mol) of NaOH in 30 ml water. The compound melts at 188°–189° C. (after recrystallisation from toluene).

Analysis (C₁₆H₃₁ClN₂O₂): calculated: C 60.27%; H 9.80%; N 8.78%; Cl 11.12%; found: C 60.46%; H 9.74%; N 8.76%; Cl 10.97%

EXAMPLE 19

The compound of the formula

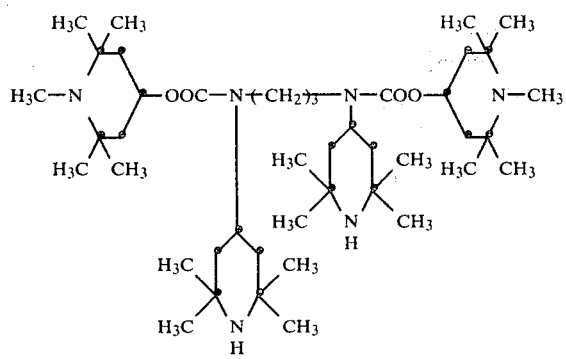

melting at 129°–130° C. (from hexane) is prepared in the same manner as described in example 16 from the hydrochloride of 1,2,2,6,6-pentamethylpiperidin-4-yl chlorocarbonate and N,N'-bis(2,2,6,6-tetramethylpiperidin-4-yl)-trimethylene-diamine.

Analysis ($C_{43}H_{82}N_6O_4$) calculated: C 69.12%; H 11.06%; N 11.25%; found: C 69.61%; H 11.03%; N 11.20%

EXAMPLE 20

The compound of the formula

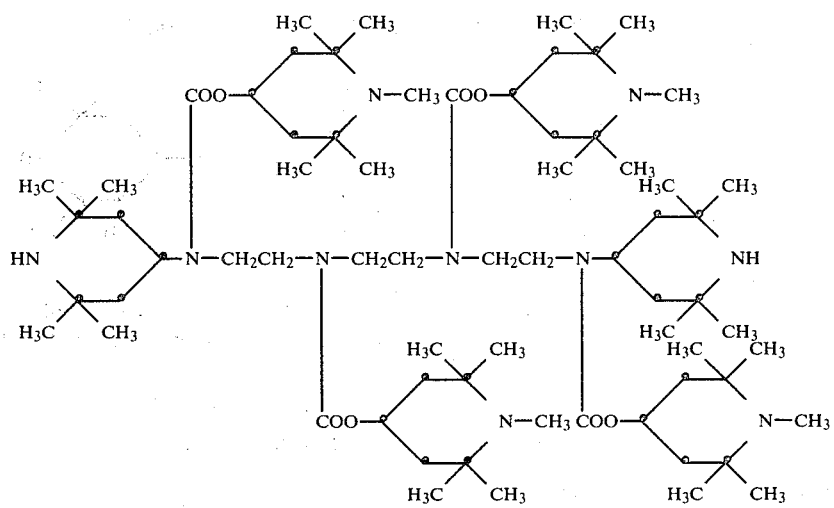

melting at 241°–242° C. (from toluene) is prepared as described in example 16 from 1,2,2,6,6-pentamethylpiperidin-4-yl chlorocarbonate and N,N'-bis(2,2,6,6-tetramethylpiperidin-4-yl)-1,8-diamino-3,6-diazaoctane.

Analysis ($C_{68}H_{128}N_{10}O_8$) calculated: C 67.29%; H 10.63%; N 11.54%; found: C 66.07%; H 10.35%; N 11.38%

As mentioned at the outset, the compounds of the formula (I) are very efficient in improving the light resistance, heat resistance and oxidation resistance of synthetic polymers, for example polyethylene of high or low density, polypropylene, ethylene/propylene copolymers, ethylene/vinyl acetate copolymers, polybutadiene, polyisoprene, polystyrene, butadiene/styrene copolymers, acrylonitrile/butadiene/styrene copolymers, polymers and copolymers of vinyl chloride and of vinylidene chloride, polyoxymethylene, polyurethanes, saturated and unsaturated polyesters, polyamides, polycarbonates, polyacrylates, alkyd resins and epoxide resins.

The compounds of the formula (I) can be employed as a mixture with the synthetic polymers in various ratios which depend on the nature of the polymer, the final use and the presence of other additives. In general, it is appropriate to employ from 0.01 to 5% by weight of the compounds of the formula (I) relative to the weight of the polymers, preferably from 0.1 to 1%.

The compounds of the formula (I) can be incorporated into the polymeric materials by various processes, such as dry mixing in the form of a powder, or wet mixing in the form of a solution or suspension, and also in the form of a masterbatch; in these operations, the synthetic polymer can be employed in the form of a powder, granules, a solution, a suspension or an emulsion. The polymers stabilised with the products of the formula (I) can be employed for the preparation of moulded articles, film, tapes, monofilament fibres, lacquers and the like.

If desired, other additives may be added to the mixtures of the compounds of the formula (I) with the synthetic polymers, examples being antioxidants, UV absorbers, nickel stabilisers, pigments, fillers, plasticisers, antistatic agents, flameproofing agents, lubricants, corrosion inhibitors and metal deactivators. Examples of the additives which can be employed in a mixture with the compounds of the formula (I) are, in particular:

phenolic antioxidants, such as, for example, 2,6-di-t-butyl-p-cresol, 4,4'-thio-bis-(3-methyl-6-t-butylphenol), 1,1,3-tris-(2-methyl-4-hydroxy-5-t-butylphenyl)-butane, octadecyl 3-(3,5-di-t-butyl-4-hydroxyphenyl)-propionate, pentaerythritol tetrakis-(3,5-di-t-butyl-4-hydroxyphenyl)-propionate, tris-(3,5-di-t-butyl-4-hydroxybenzyl) isocyanurate and tris-(4-t-butyl-3-hydroxy-2,6-dimethylbenzyl)isocyanurate;

secondary antioxidants, such as: esters of thiodipropionic acid, for example di-n-dodecyl thiodipropionate and di-n-octadecyl thiodipropionate; aliphatic sulfides and disulfides, for example di-n-dodecyl sulfide, di-n-octadecyl sulfide and di-n-octadecyl disulfide; aliphatic, aromatic and aliphatic-aromatic phosphites and thiophosphites, for example tri-n-dodecyl phosphite, tris-(nonylphenyl) phosphite, tri-n-dodecyl trithiophosphite, phenyl di-n-decyl phosphite, di-n-octadecyl pentaerythritol diphosphite, tris-(2,4-di-t-butylphenyl) phosphite and tetrakis-(2,4-di-t-butylphenyl) 4,4'-biphenylene diphosphite;

UV absorbers, for example 2-hydroxy-4-n-octyloxybenzophenone, 2-hydroxy-4-n-dodecyloxybenzophenone, 2-(2-hydroxy-3,5-di-t-butylphenyl)-5-chlorobenzotriazole, 2-(2-hydroxy-3,5-di-t-amylphenyl)-benzotriazole, 2,4-di-t-butylphenyl 3,5-di-t-butyl-4-hydroxybenzoate, phenyl salicylate, p-t-butylphenyl salicylate, 2,2'-di-n-octyloxy-5,5'-di-t-butyloxanilide, 2-ethoxy-5-t-butyl-2'-ethyl-oxanilide, 2-ethoxy-2'-ethyloxanilide and 2-ethoxy-2'-ethyl-5,5'-di-t-butyloxanilide;

polyalkylpiperidine light stabilisers, for example 2,2,6,6-tetramethylpiperidin-4-yl benzoate, bis(2,2,6,6-pentamethylpiperidin-4-yl)-sebacate, bis(1,2,2,6,6-pentamethylpiperidin-4-yl)-sebacate, bis(1,2,2,6,6-pentamethylpiperidin-4-yl)-butyl-(3,5-di-t-butyl-4-hydroxybenzyl)malonate;

nickel-based light stabilisers, for example Ni monoethyl 3,5-di-t-butyl-4-hydroxybenzyl-phosphonate, the butylamine-Ni 2,2'-thio-bis-(4-t-octylphenolate) complex, Ni 2,2'-thio-bis-(4-t-octylphenolphenolate), Ni dibutyl-dithiocarbamate, Ni 3,5-di-t-butyl-4-hydroxybenzoate and the Ni complex of 2-hydroxy-4-n-octyloxybenzophenone;

organo-tin stabilisers, for example dibutyl-tin maleate, dibutyl-tin laurate and dioctyl-tin maleate;

acrylic esters, for example ethyl α-cyano-β,β-diphenylacrylate and methyl α-cyano-β-methyl-4-methoxycinnamate;

metal salts of higher fatty acids, for example the stearates of calcium barium, cadmium, zinc, lead and nickel and the laurates of calcium, cadmium, zinc and barium;

organic and inorganic pigments, for example Colour Index Pigment Yellow 37, Colour Index Pigment Yellow 83, Colour Index Pigment Red 144, Colour Index Pigment Red 48:3, Colour Index Pigment Blue 15, Colour Index Pigment Green 7, titanium dioxide, iron oxide and the like.

The efficiency, as stabilisers, of the products prepared according to the present invention is illustrated in the examples which follow, in which some of the products obtained in the preparation examples are employed in a synthetic polymer composition.

The results are shown in comparison to those obtained by the addition of commercially available light stabilisers.

EXAMPLE 21

In each case, 2 g of one of the compounds indicated in Table 1 and 1 g of n-octadecyl 3-(3,5-di-t-butyl-4-hydroxyphenyl)-propionate (antioxidant) are intimately mixed with 1000 g of polypropylene of melt index 2.6 (Moplen T, a product of Societa Montedison, Italy) and 1 g of calcium stearate.

The mixture obtained is then extruded at a temperature of 200°–230° C. and is converted to granules from which tapes having a thickness of 50 μm and a width of 2.5 mm are produced. The working conditions are:
temperature of the extruder: 230°–240° C.
temperature of the head: 240° C.
stretch ratio: 1:6.

The tapes obtained are exposed in a Weather-Ometer 65 WR (ASTM G 27-70) with a black panel temperature of 63° C. Samples are taken out periodically and the residual tensile strength of these is measured by means of a tensometer, at constant speed; the exposure time required to halve the initial tensile strength ($T_{50}$) is then evaluated.

For comparison, a tape is prepared under the same conditions, 2 g of 2-hydroxy-4-n-octyloxybenzophenone being added as a light stabiliser.

The results obtained are shown in Table 1.

TABLE 1

| Light Stabiliser | $T_{50}$ (hours) |
| --- | --- |
| 2-Hydroxy-4-n-octyloxybenzophenone | 300 |
| Compound of Example 1 | 2320 |
| Compound of Example 2 | 2230 |
| Compound of Example 3 | 2360 |
| Compound of Example 6 | 1980 |
| Compound of Example 7 | 2330 |
| Compound of Example 9 | 1930 |
| Compound of Example 10 | 1770 |
| Compound of Example 11 | 2180 |
| Compound of Example 13 | 2040 |

EXAMPLE 22

2 g of each of the compounds listed in Table 2 were mixed thoroughly with 1000 g of a high density polyethylene of melt index 0.40 (Hostalen GF 7660, Hoechst AG, BRD), 0.5 g of n-octadecyl 3-(3,5-di-t-butyl-4-hydroxyphenyl)-propionate (as antioxidants) and 1 g of calcium stearate.

The mixture obtained was then extruded at a temperature of 190° C. and cut into granules, from which plates of 0.2 mm thickness were obtained by compression moulding at 200° C. The plates were exposed in a Weather-Ometer 65 WR with a black panel temperature of 63° C. and the increase in the content of carbonyl groups (Δ CO) was checked periodically, using non-exposed samples for compensating the initial absorption of the polymer. The exposition time (T 0.1) necessary for Δ CO=0.1% (at a wavelength of 5.85 μm) is calculated.

For comparison samples were prepared under the same conditions
(a) without addition of a light stabiliser
(b) with addition of 2 g of 2-hydroxy-4-n-octyloxybenzophenone. The results are listed in Table 2.

TABLE 2

| Light Stabiliser | T 0.1 (hours) |
| --- | --- |
| without | 320 |
| 2-Hydroxy-4-n-octyloxy-benzophenone | 1000 |
| Compound of Example 1 | 5710 |
| Compound of Example 6 | 5350 |
| Compound of Example 7 | 5280 |
| Compound of Example 9 | 5050 |

What is claimed is:

1. A compound of the formula

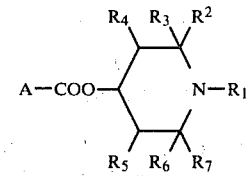

or an acid addition salt thereof, in which
$R_1$ represents
(a) hydrogen,
(b) $C_1$–$C_{12}$-alkyl,
(c) —$CH_2CN$
(d) $C_3$–$C_{12}$-alkenyl,
(e) $C_3$–$C_{12}$-alkinyl, (f) benzyl, (g) benzyl substituted by 1 to 3 $C_1$–$C_4$-alkyl radicals, (h) hydroxybenzyl, (i) hydroxybenzyl substituted by 1 to 3 $C_1$–$C_4$-alkyl radicals, (j) a —$COR_8$, —$COOR_8$, —$CH_2COOR_8$ or —$CONR_8R_9$ radical in which $R_8$ and $R_9$, which may be identical or different, represent
  (1) linear or branched $C_1$–$C_{12}$-alkyl,
  (2) $C_3$–$C_{12}$-alkenyl,
  (3) $C_5$–$C_{12}$-cycloalkyl,
  (4) phenyl,
  (5) phenyl substituted by 1 to 3 $C_1$–$C_8$-alkyl radicals,
  (6) hydroxyphenyl,
  (7) hydroxyphenyl substituted by 1 to 3 $C_1$–$C_8$-alkyl radicals,
  (8) $C_7$–$C_{12}$-aralkyl, or
  (9) 2,2,6,6-tetramethyl-piperidin-4-yl, (k) a

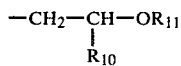

radical, in which $R_{10}$ is hydrogen, methyl or phenyl and $R_{11}$ is hydrogen, —$R_8$, —$COR_8$ or —$CONR_8R_9$, in which $R_8$ and $R_9$ are as defined above, or (l) a

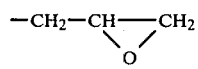

radical;

$R_2$, $R_3$, $R_6$ and $R_7$, which may be identical or different, are alkyl containing 1 to 6 C atoms;

$R_4$ and $R_5$, which may be identical or different, are hydrogen or alkyl containing 1 to 6 C atoms;

A is

radical, in which $R_{12}$ is a radical of the formula

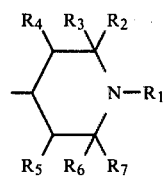

in which $R_1$, $R_2$, $R_3$, $R_4$, $R_5$, $R_6$ and $R_7$ are as defined above, $R_{13}$ is hydrogen, linear or branched $C_1$–$C_{20}$-alkyl, $C_5$–$C_{12}$-cycloalkyl, phenyl, o-, m- or p-toluyl, o-, m- or p-hydroxyphenyl, 3,5-di-t-butyl-4-hydroxy-phenyl, o-, m- or p-methoxyphenyl, o-, m- or p-ethoxyphenyl, benzyl, 4-methylbenzyl, 4-t-butylbenzyl, 4-hydroxybenzyl, 3,5-di-t-butyl-4-hydroxybenzyl, 4-methoxybenzyl, 4-ethoxybenzyl, or a group of the formula

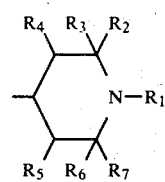

or A is a heterocyclic radical selected from the group consisting of pyrrolidin-1-yl, piperidin-1-yl, morpholin-4-yl, piperazin-1-yl, 4-methyl-piperazin-1-yl, hexahydroazepin-1-yl, homopiperazin-1-yl and 4-methyl-homopiperazin-1-yl.

2. A compound according to claim 1, in which $R_1$ represents hydrogen, $C_1$–$C_6$-alkyl, $C_3$–$C_6$-alkenyl, benzyl or $C_1$–$C_6$-acyl; $R_2$ and $R_6$ are methyl; $R_4$ is hydrogen or methyl; $R_5$ is hydrogen; $R_3$ and $R_7$ are methyl or ethyl; $R_{12}$ is a radical of the formula

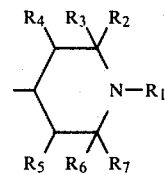

$R_{13}$ represents hydrogen, $C_1$–$C_{12}$-alkyl, $C_6$–$C_{12}$-cycloalkyl, 2,2,6,6-tetramethylpiperidin-4-yl or 1,2,2,6,6-pentamethylpiperidin-4-yl; and A represents a heterocyclic radical selected from the group of piperidin-1-yl, morpholin-4-yl.

3. A compound according to claim 2, in which $R_1$ is hydrogen, methyl, allyl, benzyl or acetyl, $R_2$, $R_3$, $R_6$ and $R_7$ are methyl, $R_4$ and $R_5$ are hydrogen, $R_{12}$ is 2,2,6,6-tetramethylpiperidin-4-yl or 1,2,2,6,6-pentamethylpiperidin-4-yl and $R_{13}$ is hydrogen, $C_4$–$C_8$-alkyl, cyclohexyl, 2,2,6,6-tetramethylpiperidin-4-yl or 1,2,2,6,6-pentamethylpiperidin-4-yl.

4. A compound according to claim 1, said compound being:

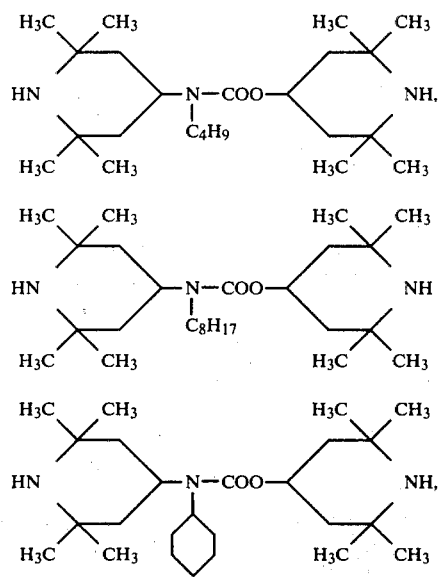

-continued
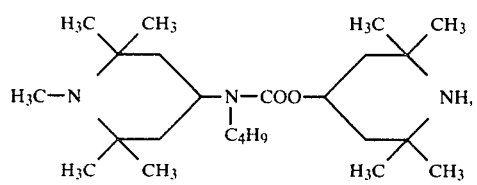
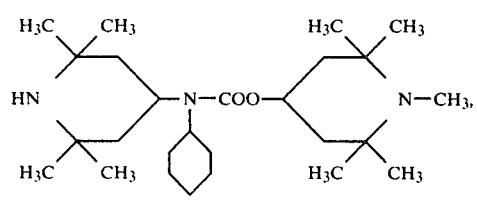
-continued
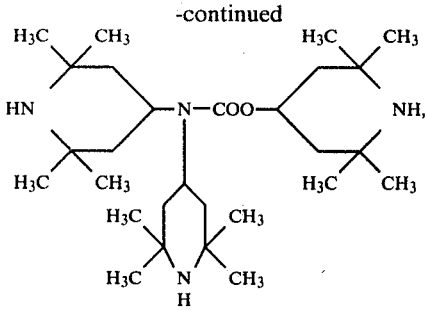
or
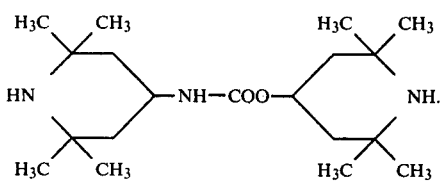
* * * * *